(12) United States Patent
Jochemsen et al.

(10) Patent No.: US 8,374,409 B2
(45) Date of Patent: Feb. 12, 2013

(54) METHOD FOR OPTICALLY IMAGING AN INTERIOR OF A TURBID MEDIUM, METHOD FOR RECONSTRUCTING AN IMAGE OF AN INTERIOR OF A TURBID MEDIUM, DEVICE FOR IMAGING AN INTERIOR OF A TURBID MEDIUM, MEDICAL IMAGE ACQUISITION DEVICE AND COMPUTER PROGRAM

(75) Inventors: Robert Jochemsen, Eindhoven (NL); Tim Nielsen, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 760 days.

(21) Appl. No.: 12/519,852

(22) PCT Filed: Dec. 17, 2007

(86) PCT No.: PCT/IB2007/055150
§ 371 (c)(1),
(2), (4) Date: Jun. 18, 2009

(87) PCT Pub. No.: WO2008/075278
PCT Pub. Date: Jun. 26, 2008

(65) Prior Publication Data
US 2010/0040267 A1 Feb. 18, 2010

(30) Foreign Application Priority Data
Dec. 21, 2006 (EP) .................................. 06126881

(51) Int. Cl.
*G06K 9/00* (2006.01)
(52) U.S. Cl. ........................................ 382/128; 382/131
(58) Field of Classification Search .................. 382/128, 382/131, 132; 600/442, 476
See application file for complete search history.

(56) References Cited

U.S. PATENT DOCUMENTS

| | | | | |
|---|---|---|---|---|
| 5,719,398 A * | 2/1998 | Colak | ......................... | 250/341.1 |
| 5,903,357 A * | 5/1999 | Colak | ........................... | 356/432 |
| 5,994,690 A * | 11/1999 | Kulkarni et al. | ............... | 250/216 |
| 6,064,073 A | 5/2000 | Hoogenraad | | |
| 6,175,759 B1 * | 1/2001 | Chan et al. | ..................... | 600/431 |
| 6,529,770 B1 * | 3/2003 | Grimblatov | .................... | 600/479 |
| 7,412,024 B1 * | 8/2008 | Yun et al. | ......................... | 378/37 |

(Continued)

FOREIGN PATENT DOCUMENTS

| | | |
|---|---|---|
| WO | 9966832 A1 | 12/1999 |
| WO | 0241760 A2 | 5/2002 |

(Continued)

OTHER PUBLICATIONS

Gao et al (Efefcts of background fluorescence in fluorescence molecular tomography); Sep. 2005.*

(Continued)

*Primary Examiner* — Chan S Park
*Assistant Examiner* — Nancy Bitar (57) ABSTRACT

The invention relates to a method of imaging an interior of a turbid medium, a device for imaging an interior of a turbid medium, and a medical image acquisition device. A turbid medium is accommodated in a receiving volume (5), light from a light source is coupled into (10) and out of the receiving volume and detected (15) after which a dataset is obtained from the detected light (20). The dataset is then communicated to an image reconstruction algorithm (30) and an image of an interior of the turbid medium is reconstructed based on the detected light (35). According to the invention the dataset is changed prior to communicating the dataset to the image reconstruction algorithm into a further dataset (25), with a further dataset satisfying an input assumption underlying the image reconstruction algorithm.

18 Claims, 3 Drawing Sheets

U.S. PATENT DOCUMENTS

| | | |
|---|---|---|
| 2002/0190212 A1 | 12/2002 | Boas |
| 2003/0135122 A1* | 7/2003 | Bambot et al. ............... 600/476 |
| 2003/0195417 A1* | 10/2003 | Wake et al. ................ 600/431 |
| 2006/0149479 A1* | 7/2006 | Ma .............................. 702/19 |

FOREIGN PATENT DOCUMENTS

| | | |
|---|---|---|
| WO | 2005083396 A1 | 9/2005 |
| WO | 2006069444 A1 | 7/2006 |
| WO | 2007060571 A1 | 5/2007 |

OTHER PUBLICATIONS

Gao et al: "Effects of Background Fluorescence in Fluorescence Molecular Tomography"; Applied Optics, vol. 44, No. 26, Sep. 10, 2005.

* cited by examiner

METHOD FOR OPTICALLY IMAGING AN INTERIOR OF A TURBID MEDIUM, METHOD FOR RECONSTRUCTING AN IMAGE OF AN INTERIOR OF A TURBID MEDIUM, DEVICE FOR IMAGING AN INTERIOR OF A TURBID MEDIUM, MEDICAL IMAGE ACQUISITION DEVICE AND COMPUTER PROGRAM

FIELD OF INVENTION

The invention relates to a method for optically imaging an interior of a turbid medium employing an image reconstruction algorithm The invention also relates to a method for reconstructing an image of an interior of a turbid medium.

The invention also relates to a device for imaging an interior of a turbid medium.

The invention also relates to a medical image acquisition device.

The invention also relates to computer program products for use in the abovementioned methods and devices.

BACKGROUND OF THE INVENTION

An embodiment of methods and devices of this kind is known from European patent application 05111164.9. The described method and device can be used for imaging an interior of a turbid medium, such as biological tissue using diffuse optical tomography. In medical diagnostics, the method and device may be used for imaging, for instance, an interior of a female breast. The receiving volume receives a turbid medium, such as a breast. Next, light from the light source is coupled into the receiving volume. This light is chosen to excite a fluorescent agent comprised in the receiving volume. When imaging an interior of, for instance, a female breast, the light chosen to excite a fluorescent agent comprised in the receiving volume typically has a wavelength within the range of 400 nm to 950 nm.

Light emanating from the receiving volume as a result of coupling light from the light source into the receiving volume is detected through use of a photodetector unit. A dataset based on the detected light is then communicated to a image reconstruction unit which then reconstructs an image of an interior of the turbid medium, for instance a female breast, based on the detected light. Instead of choosing the light from the light source to excite a fluorescent agent comprised in the receiving volume, the light from the light source may be chosen such that it is capable of propagating through the turbid medium to enable a transmission examination of a turbid medium. In a transmission examination light from the light source is coupled into the turbid medium, passes through the turbid medium without exciting a fluorescent agent that may be present, and is detected after having passed through the turbid medium. When imaging an interior of a female breast in a transmission examination, light having a wavelength within the range of 400 nm to 1400 nm is typically used. Light emanating from the receiving volume as a result of coupling light from the light source into the receiving volume is again detected through use of the photodetector unit. The dataset based on the detected light is then communicated to the image reconstruction unit and used to reconstruct an image of an interior of the turbid medium based on the detected light. It is a characteristic of the known method and device that small and low contrast elements comprised in a medium are sometimes difficult to image.

SUMMARY OF THE INVENTION

It is an object of the invention to improve the quality of a reconstructed image in order to improve the detectability of small and low contrast elements comprised in a turbid medium. According to the invention this object is realized by the image reconstruction algorithm operating on a dataset satisfying an input assumption underlying the image reconstruction algorithm. Therefore in a first aspect the invention relates to a method for optically imaging an interior of a turbid medium (100) employing an image reconstruction algorithm, wherein the image reconstruction algorithm operates on a dataset satisfying an input assumption underlying the image reconstruction algorithm.

The invention is based on the recognition that the quality of a reconstructed image is negatively affected if a dataset is communicated to an image reconstruction algorithm with the dataset not satisfying an input assumption comprised in the image reconstruction algorithm. Suppose an image reconstruction algorithm is used to reconstruct an image of an interior of a medium comprising a homogeneously distributed fluorescent agent, with the fluorescent agent to be excited by excitation light from a light source. Suppose further that an obtained dataset comprises the ratio of the intensity of fluorescence light and transmitted excitation light (that is a part of the excitation light that has passed through the medium without exciting the fluorescent agent comprised in the medium) emanating from a receiving volume comprising the medium as measured at different distances between a position at which excitation light from the light source is coupled into the receiving volume and a position at which fluorescence and transmitted excitation light emanate from the receiving volume. Suppose still further that underlying the image reconstruction algorithm is the assumption that the ratio of the intensity of the fluorescence light and transmitted laser light increases linearly as a function of the distance between the position at which excitation light from the light source is coupled into the receiving volume and a position at which fluorescence and transmitted excitation light emanate from the receiving volume, whereas in reality the trend increases more than linear. An explanation of the background of the assumption is given at the end of this section. As a result of the fact that a linear relationship is assumed whereas in reality the relationship is more than linear, the image reconstruction algorithm will then 'see' more fluorescence light than it should as the distance between the position at which excitation light from the light source is coupled into the receiving volume and a position at which fluorescence and transmitted excitation light emanate from the receiving volume increases. This is because the image reconstruction algorithm expects the ratio of the fluorescence light and transmitted laser light to increase linearly, whereas in the measured data the ratio increases more than linearly. Thus the image reconstruction algorithm will reconstruct too much fluorescence at greater distances between a position at which light from the light sources coupled into the receiving volume and a position at which fluorescence light emanates from the receiving volume. A possible solution to this problem is to change the assumption underlying the image reconstruction. However, this is often very complex and time-consuming. The invention presents an easier method by changing the dataset such that it satisfies the assumption underlying the image reconstruction algorithm. In the example given above, the method according to the invention would map the dataset having a more than linear trend onto a linear trend.

To conclude this section, it will now be explained how, in the example given above, one can arrive at the assumption that the ratio of the intensity of the fluorescence and transmitted excitation light increases linearly as a function of the distance between the position at which excitation light from the light source is coupled into a receiving volume comprising an optically turbid medium comprising a fluorescent agent and the position at which fluorescence and transmitted excitation light emanate from the receiving volume. The basic solution to the forward problem faced in reconstructing an image of an interior of an optically turbid medium comprising a fluorescent agent based on detected fluorescence and transmitted excitation light and using an image reconstruction algorithm is to solve a diffusion equation describing the propagation of light through the medium. However, this is often very complex and time-consuming. One approach to simplify the problem is to use the Born approximation. In this approximation the following model is used to explain the ratio of the intensity of fluorescence light and transmitted excitation light as a function of the distance between the position of a source of excitation light and a position at which fluorescence and transmitted excitation light are detected. Excitation light travels from a position at which the excitation light is coupled into the medium to a position at which a fluorescent agent is located. Fluorescence light resulting from the interaction between the excitation light and the fluorescent agent at this position then travels from this position to a position at which the fluorescence light is detected. However, not all of the excitation light will actually excite the fluorescent agent. Some of the excitation light will reach the position at which it is detected without causing fluorescence. If one then integrates the contributions of fluorescence light and transmitted excitation light over all possible positions in the medium one arrives at the overall ratio of the intensity of fluorescence and transmitted excitation light for a given detection position. It is well known that for an infinite homogeneous medium the intensity of light decreases exponentially as a function of distance with a certain attenuation factor as parameter. The attenuation factor takes into account light attenuating processes such as absorption and excitation. Excitation of a fluorescent agent causes the intensity of excitation light exciting the fluorescent agent to decrease. Using the Born approximation and with $k_x$ being the attenuation factor for excitation light, $k_f$ being the attenuation factor for fluorescence light, $c(x)$ being the concentration of the fluorescent agent as a function of position, s the position of a source of excitation light, d the position of a detector for detecting fluorescence and transmitted excitation light, and $d(q,p)$ the distance between a position q and a position p, this leads to the following equation (for more information see also Ntziachristos and Weissleder, 'Experimental three-dimensional fluorescence reconstruction of diffuse media by use of a normalized Born approximation', *Optics Letters*, vol. 26, No. 12, Jun. 15, 2001, pp. 893-895):

$$\frac{I_f}{I_x} = \int \frac{e_x^{-kd(x,s)} c(x) e_f^{-kd(x,d)}}{e_x^{-kd(s,d)}} dx$$

Assuming $c(x)$ is a constant and doing the integral, the this equation becomes:

$$\frac{I_f}{I_x} = c \frac{1 - e_{fx}^{-(k-k)d(s,d)}}{k_f - k_x}$$

For small values of $k_f$-$k_x$ the exponential can be expanded into a power series showing that in that case the ratio of the intensity of fluorescence and transmitted excitation light increases with $d(s,d)$. This means that the ratio of the fluorescence and transmitted excitation light increases linearly as the distance between a source position and a detection position increases with the strength of the increase being determined by the concentration of the fluorescent agent. This is exactly the kind of assumption underlying the image reconstruction algorithm in the example given in this section. For larger values of $k_f$-$k_x$ the expected behavior will be nonlinear.

With increasing concentration of the fluorescent agent processes such as the absorption of excitation light by the fluorescent agent and self absorption of fluorescence light by the fluorescent agent become increasingly important. The expected dependency of the ratio of the fluorescence and transmitted excitation light on the distance between the position of a source of excitation light and a detection position for fluorescence and transmitted excitation light will then be nonlinear.

The object of the invention is further realized with a method for reconstructing an image of an interior of a turbid medium based on a dataset obtained by detecting light emanating from a receiving volume as a result of coupling light from a light source into the receiving volume with the receiving volume comprising the turbid medium and with the method employing an image reconstruction algorithm, wherein the dataset is changed into a further dataset, with the further dataset satisfying an input assumption underlying the image reconstruction algorithm and with the further dataset to be communicated to the image reconstruction algorithm.

An embodiment of the method according to the invention is characterized in that the dataset, as a function of a chosen variable, has a measured trend, in that the input assumption requires a dataset to have a required trend as a function of the chosen variable, and in that the dataset is changed into the further dataset by mapping the dataset onto the required trend. This embodiment has the advantage that it enables a dataset to be changed into a further dataset that satisfies an input assumption underlying the image reconstruction algorithm in situations in which the input assumption implies that there is a specific dependence, for instance, a linear dependence of the dataset on the chosen variable.

A further embodiment of the method according to the invention is characterized in that a parameterized function of the chosen variable is fitted to the dataset, and in that the thus determined value of at least one parameter is subsequently used for the required trend. There can be situations in which the measured trend and the assumed trend depend on one or more shared variables. In the example given in the summary of the invention, for instance, both the measured exponential trend and the assumed linear trend depend on the concentration of a fluorescent agent comprised in a medium. The present embodiment has the advantage that by properly choosing a parameterized function for fitting to the dataset, the required trend corresponding to a particular situation can be determined. In the example referred to above, properly choosing a parameterized function would mean that the parameterized function is chosen such that the concentration of the fluorescent agent can be determined from the parameters comprised in the parameterized function. The main idea of the invention is to map the measured data trend to a data trend that is expected by the image reconstruction algorithm. The expected data trend is known since the reconstructor is made for a certain model of how the light behaves in the system. This model implicitly defines the expected data trend.

A further embodiment of the method according to the invention is characterized in that the reconstruction algorithm is based on the Born approximation. The Born approximation is often used in image reconstruction algorithms. As it is an approximation, assumptions comprised in an image reconstruction algorithm using the Born approximation are not always satisfied in reality. This embodiment has the advantage that it enables to improve the quality of an image reconstructed through use of an algorithm that comprises an approximation that is often used.

A further embodiment of the method according to the invention is characterized in that the light from the light source is chosen to excite a fluorescent agent comprised in the receiving volume, in that the photodetector unit is arranged for detecting fluorescence light emanating from the receiving volume as a result of coupling light from the light source into the receiving volume, and in that the dataset comprises data relating to the detected fluorescence light. This embodiment has the advantage that it solves the particular problem of too much or too little fluorescence being indicated in a reconstructed image as illustrated in the summary of the invention.

A further embodiment of the method according to the invention is characterized in that the further dataset is changed into a contrast enhanced dataset by removing at least a part of the required trend from the further dataset. This embodiment has the advantage that the contrast in an image reconstructed according to the method according to the invention is enhanced by removing at least a part of the required trend from the further dataset. Removing, for instance, p percent of the required trend from the further dataset removes p percent of the background on which the data of the further dataset sits.

A further embodiment of the method according to the invention is characterized in that the turbid medium comprises biological tissue. This embodiment has the advantage that it enables the examination of biological tissue.

A further embodiment of the method according to the invention is characterized in that medium comprises a mammalian breast. This embodiment has the advantage that it enables examining, for instance, a human female breast in order to detect lesions such as potential tumors.

The object of the invention is further realized with a device for imaging an interior of a turbid medium comprising:

a receiving volume for accommodating the turbid medium;

a light source for generating light to be coupled into the receiving volume;

a photodetector unit for detecting light emanating from the receiving volume as a result of coupling light from the light source into the receiving volume;

an image reconstruction unit for reconstructing an image of an interior of the turbid medium based on the detected light, characterized in that the device further comprises:

a data processing unit for carrying out the method according to any one of the previous embodiments. This embodiment has the advantage that a device for imaging an interior of a turbid medium would benefit from any one of the previous embodiments of the method according to the invention.

The object of the invention is further realized with a medical image acquisition device comprising:

a receiving volume for accommodating the turbid medium;

a light source for generating light to be coupled into the receiving volume;

a photodetector unit for detecting light emanating from the receiving volume as a result of coupling light from the light source into the receiving volume;

an image reconstruction unit for reconstructing an image of an interior of the turbid medium based on the detected light, characterized in that the device further comprises:

a data processing unit for carrying out the method according to any one of the previous embodiments. This embodiment has the advantage that a medical image acquisition device would benefit from any one of the previous embodiments of the method according to the invention.

The object of the invention is further realized with a computer program product comprising instructions to:

access a dataset satisfying an input assumption underlying an image reconstruction algorithm;

applying the image reconstruction algorithm to the accessed dataset.

The advantages of a computer program product according to the invention have already been mentioned in relation to any one of the embodiments of the methods according to the invention.

The object of the invention is further realized with a computer program product for causing a processor to change a dataset prior to communicating the dataset to an image reconstruction algorithm into a further dataset, with the further dataset satisfying an input assumption underlying the image reconstruction algorithm and with the dataset, the further dataset, and the image reconstruction algorithm being used in a method according to any one of the previous embodiments. The advantages of a computer program product according to the invention have already been mentioned in relation to any one of the embodiments of the methods according to the invention.

BRIEF DESCRIPTION OF THE DRAWINGS

These and other aspects of the invention will be further elucidated and described with reference to the drawings, in which.

DETAILED DESCRIPTION OF EMBODIMENTS

Figure 1:
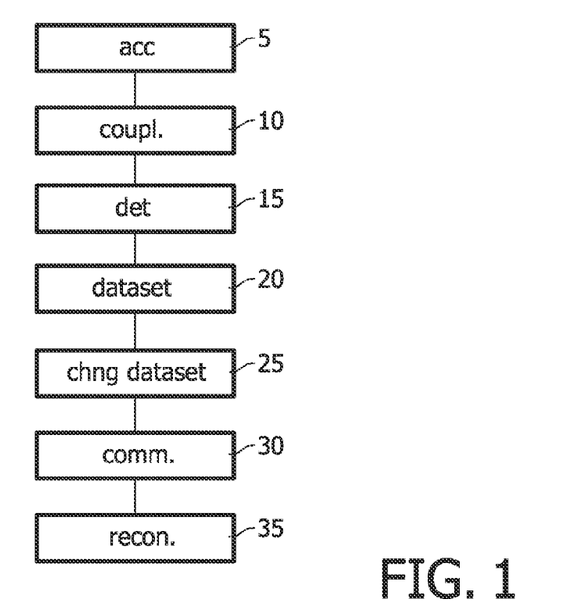
FIG. 1 illustrates an embodiment of the method of imaging an interior of a turbid medium according to the invention.

FIG. 1 illustrates an embodiment of the method of imaging an interior of a turbid medium according to the invention. In step 5 the turbid medium is accommodated inside a receiving volume. Next, in step 10, light from a light source is coupled into the receiving volume. The light from the light source is chosen to excite a fluorescent agent comprised in the turbid medium. Alternatively, the light from the light source may be chosen such that the light is able to propagate through the turbid medium without giving rise to fluorescence light. Light emanating from the receiving volume as a result of coupling light from the light source into the receiving volume is detected through use of a photodetector unit. This is done in step 15. On the basis of the detected light a dataset is obtained in step 20. The dataset may, for instance, comprised data relating to the intensity of fluorescence light emanating from the receiving volume as a function of the distance between the position at which light from the light sources coupled into the receiving volume and a position at which fluorescence light emanates from the receiving volume. According to the invention, the dataset is changed into a further dataset such that the further dataset satisfies an input assumption comprised in the image reconstruction algorithm. Changing the dataset into the further dataset is done in step 25. This can be done using software. In step 30, the further dataset is then communicated to the image reconstruction algorithm. Finally, in step 35, an image of an interior of the turbid medium is reconstructed through use of an image reconstruction unit and using the further dataset.

Figure 2:
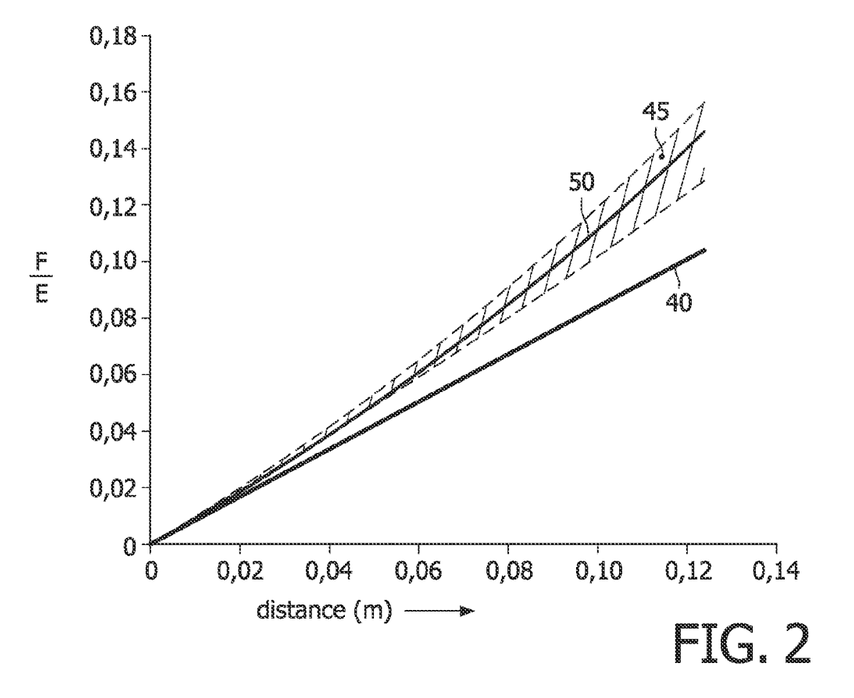
FIG. 2 illustrates changing a dataset into a further dataset satisfying an input assumption of an image reconstruction algorithm.

FIG. 2 illustrates changing a dataset into a further dataset satisfying an input assumption of an image reconstruction algorithm. Plotted along the horizontal axis is the distance in meters between the position at which light from a light source enters a receiving volume, with a light from the light source being chosen to excite a fluorescent agent comprised in the receiving volume, and a position at which fluorescence light emanates from the receiving volume. Plotted along the vertical axis is the ratio between the intensities of fluorescence light and excitation light emanating from the receiving volume. Using the Born approximation, an image reconstruction algorithm has the input assumption that the ratio of the intensities of the fluorescence light and the excitation light emanating from the receiving volume is a linearly increasing function of the distance between the position at which excitation light is coupled into the receiving volume and a position at which fluorescence light and excitation light emanate from the receiving volume. In principle, this assumption is reasonable as a larger distance implies a larger volume in which the fluorescent agent can be excited. The assumption of the linear relationship is a consequence of the assumption that the excitation light and the fluorescence light experience the same attenuation within the receiving volume. In FIG. 2 the linear relationship between the ratio of the intensities of the fluorescence light and the excitation light is illustrated by the straight line 40. However, when measuring the ratio of the intensities of fluorescence light and excitation light emanating from a receiving volume comprising a homogeneously distributed fluorescent agent, it turned out that the obtain data points to not follow the straight line 40, but lie in the dashed region 45. Instead of being linear, the trend of the data points within the region 45 is rather exponential. The exponential trend results from the fact that, contrary to the early assumption, the attenuation within a receiving volume is not the same for the excitation and the fluorescence light. As a result, the input assumption for the image reconstruction algorithm that the ratio of the intensities of the fluorescence light and excitation light emanating from the receiving volume is a linear function of distance does not hold. A possible solution to this situation is to adapt the image reconstruction algorithm such that it takes into account the difference in attenuation for the excitation and the fluorescence light. In other words, a possible solution is to let go of the input assumption of the ratio of the intensities of the fluorescence and excitation like being a linear function with the distance. However, adapting an image reconstruction, algorithm is complex. The invention presents an alternative solution. According to the invention, the data points comprised in the region 45 are mapped onto the linear trend illustrated by the straight line 40. In one embodiment according to the invention this is achieved by fitting a parameterized function, having the distance between the position at which excitation light is coupled into the receiving volume and a position at which fluorescence light and excitation light emanate from the receiving volume as a variable, to the data points comprised in the region 45. In FIG. 2 the parameterized function is illustrated by curve 50. Next, the data points comprised in the region 45 can be mapped onto the straight line 40 by subtracting the curve 50 from the data points and adding the straight line 40. As an alternative the data can be divided by the ratio of the two trend curves. This has the advantage that the sign of the data cannot change by the resealing. According to the invention of the value of a parameter determined by fitting the parameterized function to the data points may be used to determine a parameter of the assumed relationship. In this example this means, for instance, that by fitting a parameterized function to the data points the concentration of the fluorescent agent comprised in the receiving volume is determined, with the concentration of the fluorescent agent being a parameter of the parameterized function. The determined concentration then determines the slope of the straight line 40. It stands to reason that the slope of the straight line 40 increases as the concentration of the fluorescent agent comprised in the receiving volume increases. This is true because the amount of fluorescence light does not only increase with increasing distance and hence increasing volume in which fluorescence light is generated between positions at which light is coupled into and out of the receiving volume, but also with the concentration of the fluorescent agent comprised within this volume.

Figure 3:
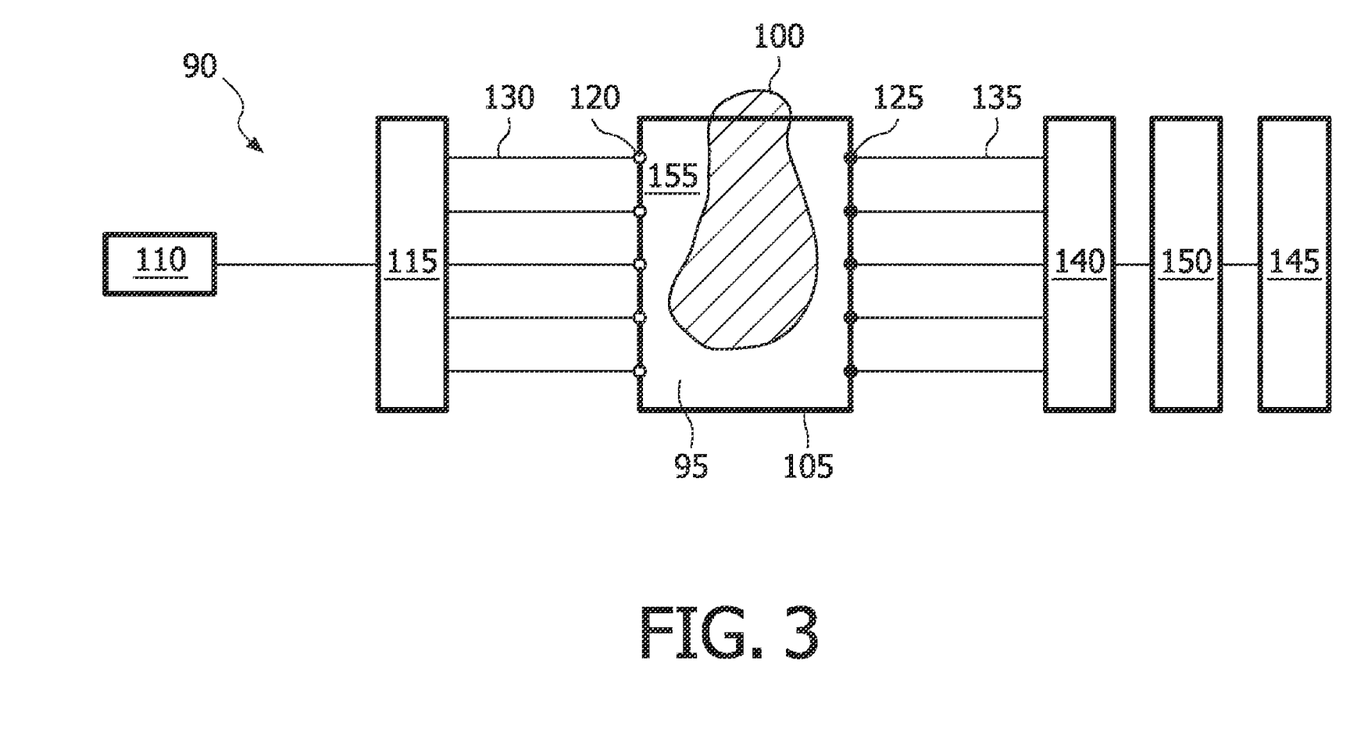
FIG. 3 schematically shows an embodiment of a device for imaging an interior of a turbid medium according to the invention.

FIG. 3 schematically shows one embodiment of a device for imaging an interior of a turbid medium according to the invention. The device 90 is suitable for carrying out diffuse optical tomography measurements. The device 90 comprises a receiving volume 95 for receiving a turbid medium 100. The receiving volume 95 is limited by a wall 105. Light from an irradiation light source 110 is coupled into the receiving volume 95 through use of the selection unit 115. The light from the light source 110 is chosen to excite a fluorescent agent comprised in the turbid medium 100. Alternatively, the light from the light source 110 may be chosen such that it can propagate through the turbid medium 100 without giving rise to fluorescence light. In medical diagnostics, where the device 90 may be used for imaging, for instance, an interior of a female breast, light having a wavelength within the range of, for instance, 600 nm to 1400 nm is suitable for this purpose. The selection unit at 115 is used to successively select an entrance positioned for light from a plurality of entrance positions for light 120. Light emanating from the receiving volume 95 as a result of coupling light from the irradiation light source 110 into the receiving volume 95 exits to the receiving volume 95 using a plurality of exit positions for light of 125. Light emanating from the receiving volume 95 is detected through use of a photodetector unit 140. The plurality of entrance positions for light 120 are optically coupled to the selection unit 115 using light guides 130. The plurality of exit positions for light 125 is optically coupled to the photodetector unit 140 using light guides 135. Image reconstruction unit 145 is used to reconstruct an image of an interior of the turbid medium 100 based on the detected light. According to the invention, the device 90 further comprises a data processing unit 150 for carrying out the method according to any one of the embodiment of the method according to the invention. Inside the receiving volume 95, the turbid medium 100 may be surrounded by a matching medium 155. The matching medium 155 has optical properties, such as absorption coefficient, similar to those of the turbid medium 100. In this way, boundary effects stemming from coupling light from the irradiation light source 110 into and out of the turbid medium 100 are reduced and optical short-circuits around the turbid medium 100 prevented. In FIG. 3 the receiving volume 95 is bound by a wall 105. However, this need not always be the case. Another embodiment of a device for imaging an interior of a turbid medium is that of a handheld device that may, for instance, be pressed against a side of a turbid medium. In that case, the measurement volume is the volume occupied by the part of the turbid medium from which light is detected as a result of irradiating the turbid medium.

Figure 4:
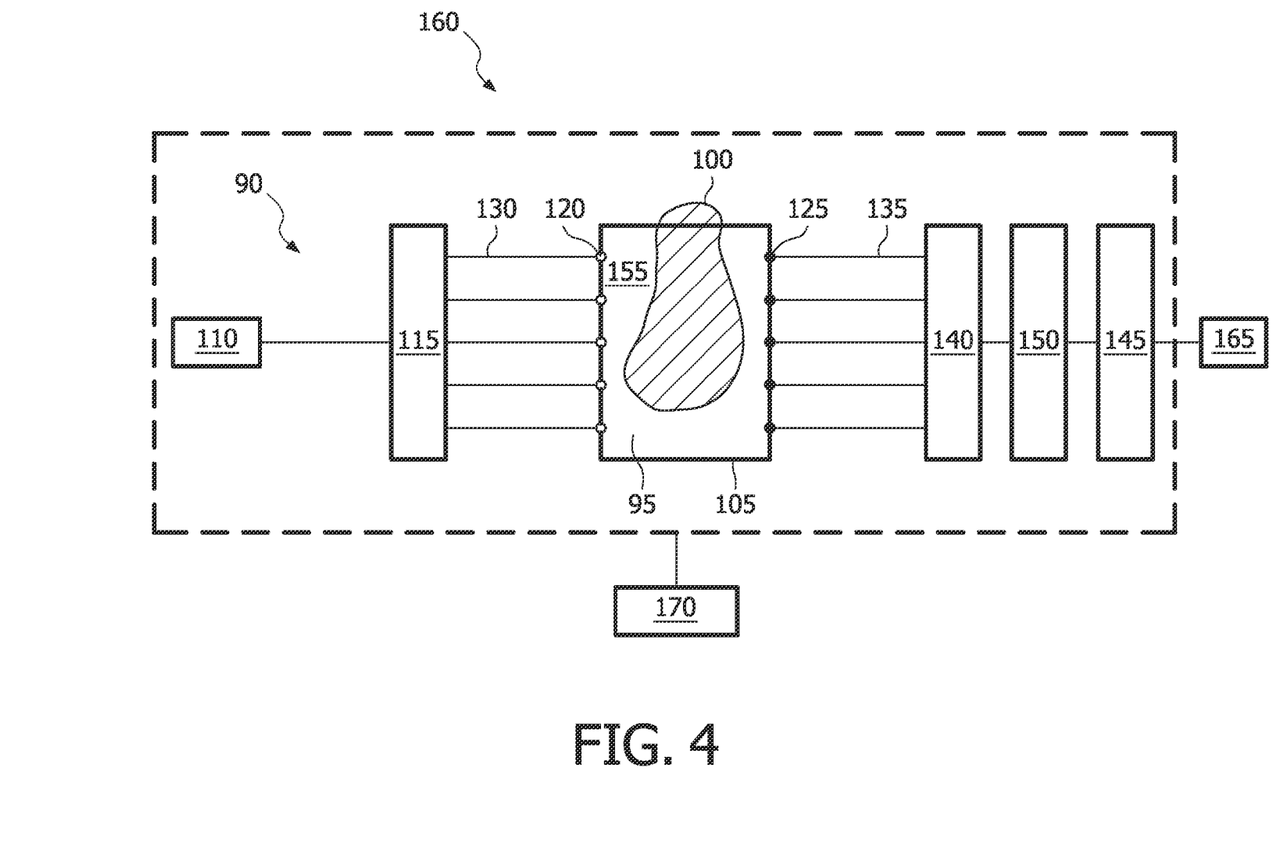
FIG. 4 schematically shows an embodiment of a medical image acquisition device according to the invention.

FIG. 4 schematically shows an embodiment of a medical image acquisition device according to the invention. The medical image acquisition device 160 comprises the elements of the device 90 shown in FIG. 3 as indicated by the dashed square. Additionally, the medical image acquisition device 160 further comprises a screen in 165 for displaying a reconstructed image of an interior of the turbid medium 100 and an operator interface 170, such as the keyboard, allowing an operator to interact with a the medical image acquisition device 160.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements, and by means of a suitably programmed computer. In the system claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:

1. A method of processing a dataset, executable by a data processor, for reconstructing an image of an interior of a turbid medium using an image reconstruction algorithm, the dataset being obtained by detecting light emanating from a receiving volume as a result of coupling light from a light source into the receiving volume with the receiving volume comprising the turbid medium, the method comprising:

changing the dataset into a further dataset satisfying an input assumption underlying the image reconstruction algorithm, the dataset having a measured trend as a function of a chosen variable, and the input assumption requiring the dataset to have a required trend as a function of the chosen variable, wherein changing the dataset into the further dataset comprises mapping the dataset onto the required trend;

changing the further dataset into a contrast enhanced dataset by removing at least a part of the required trend from the further dataset; and communicating at least one of the further dataset and the contrast enhanced dataset to an image reconstruction unit for reconstructing the image using the image reconstruction algorithm.

2. The method according to claim 1, wherein removing a percentage of the required trend from the further dataset removes a corresponding percentage of background on which data of the further dataset sits.

3. The method according to claim 1, wherein a parameterized function of the chosen variable is fitted to the dataset, and wherein a value of at least one parameter is determined by fitting the parameterized function to the dataset, the at least one parameter being used for the required trend.

4. The method according to claim 1, wherein the image reconstruction algorithm is based on the Born approximation.

5. The method according to claim 1, wherein the light from the light source is chosen to excite a fluorescent agent comprised in the receiving volume, the method further comprising:

detecting fluorescence light emanating from the receiving volume as a result of coupling light from the light source into the receiving volume, wherein the dataset comprises data relating to the detected fluorescence light.

6. The method according to claim 1 applied to biological tissue.

7. The method according to claim 6 applied to a mammalian breast.

8. A device for imaging an interior of a turbid medium, the device comprising:

a receiving volume for accommodating the turbid medium;

a light source for generating light to be coupled into the receiving volume;

a photodetector unit for detecting light emanating from the receiving volume as a result of coupling light from the light source into the receiving volume, providing a dataset based on the detected light;

an image reconstruction unit for reconstructing an image of an interior of the turbid medium, using an image reconstruction algorithm; and a data processing unit for changing the dataset provided by the photo detector unit to a further dataset that satisfies an input assumption underlying the image reconstruction algorithm, the dataset having a measured trend as a function of a chosen variable, and the input assumption requiring the dataset to have a required trend as a function of the chosen variable, for changing the further dataset into a contrast enhanced dataset by removing at least a part of the required trend from the further dataset, and for communicating the further dataset to the image reconstruction unit for reconstructing the image using the image reconstruction algorithm, wherein changing the dataset into the further dataset comprises mapping the dataset onto the required trend.

9. A medical image acquisition device comprising: the device for imaging an interior of a turbid medium according to claim 8.

10. The device according to claim 8, wherein the receiving volume is limited by a wall, wherein the wall defines a plurality of entrance positions for passing light received from the light source and a plurality of exit positions for passing light emanating from the receiving volume.

11. The device according to claim 10, further comprising:

a selection unit for successively selecting an entrance position of the plurality of entrance positions for passing the light from the light source.

12. The device according to claim 8, wherein a parameterized function of the chosen variable is fitted to the dataset, and wherein a value of at least one parameter is determined by fitting the parameterized function to the dataset, the at least one parameter being used for the required trend.

13. The device according to claim 8, wherein the image reconstruction algorithm is based on the Born approximation.

14. The device according to claim 8, wherein the light from the light source is chosen to excite a fluorescent agent comprised in the receiving volume, and wherein the photodetector unit further detects fluorescence light emanating from the receiving volume as a result of coupling light from the light source into the receiving volume, the dataset comprising data relating to the detected fluorescence light.

15. A non-transitory computer readable medium storing a program, executable by a processor, for reconstructing an image of an interior of a turbid medium, the dataset having been obtained by detecting light emanating from a receiving volume as a result of coupling light from a light source into the receiving volume with the receiving volume comprising a turbid medium, the computer readable medium comprising:

changing code for changing the dataset into a further dataset satisfying an input assumption underlying the image reconstruction algorithm, the dataset having a measured trend as a function of a chosen variable, and the input assumption requiring the dataset to have a required trend as a function of the chosen variable, wherein changing the dataset into the further dataset comprises mapping the dataset onto the required trend, the further dataset being communicated to an image reconstruction unit for reconstructing the image using the image reconstruction algorithm; and changing code for changing the further dataset into a contrast enhanced dataset by removing at least a part of the required trend from the further dataset.

16. The computer readable medium according to claim 15, wherein a parameterized function of the chosen variable is fitted to the dataset, and wherein a value of at least one parameter is determined by fitting the parameterized function to the dataset, the at least one parameter being used for the required trend.

17. The computer readable medium according to claim 15, wherein the image reconstruction algorithm is based on the Born approximation.

18. The computer readable medium according to claim 15, wherein the light from the light source is chosen to excite a fluorescent agent comprised in the receiving volume, and wherein fluorescence light is detected emanating from the receiving volume as a result of coupling light from the light source into the receiving volume, the dataset comprising data relating to the detected fluorescence light.

* * * * *